(12) United States Patent
Murigneux et al.

(10) Patent No.: US 8,198,511 B2
(45) Date of Patent: Jun. 12, 2012

(54) MAIZE HAVING IMPROVED DIGESTIBILITY

(75) Inventors: Alain Murigneux, La Roche Blanche (FR); Jean-Pierre Martinant, Vertaizon (FR); Christophe Tatout, Salt en Donzy (FR)

(73) Assignee: Biogemma, Paris (FR)

( * ) Notice: Subject to any disclaimer, the term of this patent is extended or adjusted under 35 U.S.C. 154(b) by 143 days.

(21) Appl. No.: 12/671,266

(22) PCT Filed: Jul. 29, 2008

(86) PCT No.: PCT/EP2008/059909
§ 371 (c)(1),
(2), (4) Date: Mar. 24, 2010

(87) PCT Pub. No.: WO2009/016166
PCT Pub. Date: Feb. 5, 2009

(65) Prior Publication Data
US 2010/0203196 A1 Aug. 12, 2010

(30) Foreign Application Priority Data
Jul. 31, 2007 (FR) ...................................... 07 05601

(51) Int. Cl.
*A01H 5/10* (2006.01)
*A01H 5/00* (2006.01)
*C12N 15/00* (2006.01)

(52) U.S. Cl. ..... 800/291; 800/278; 800/295; 800/300.1; 800/260; 800/275

(58) Field of Classification Search .................. None
See application file for complete search history.

(56) References Cited

U.S. PATENT DOCUMENTS
6,211,432 B1   4/2001   Boudet et al.

FOREIGN PATENT DOCUMENTS
| CA | 2067317 A1 | 12/1992 |
| EP | 0516958 A2 | 12/1992 |
| WO | WO-93/05159 A1 | 3/1993 |
| WO | WO-93/05160 A1 | 3/1993 |
| WO | WO-97/12982 A1 | 4/1997 |
| WO | WO-99/24561 A2 | 5/1999 |
| WO | WO-01/95702 A1 | 12/2001 |
| WO | WO-03/008585 A2 | 1/2003 |

OTHER PUBLICATIONS

Halpin, C., et al., "Manipulation of lignin quality by downregulation of cinnamyl alcohol dehydrogenase," The Plant Journal, 1994, vol. 6, No. 3, pp. 339-350.
Halpin, C., et al., "Brown-midrib maize (bm1)—a mutation affecting the cinnamyl alcohol dehydrogenase gene," The Plant Journal, 1998, vol. 14, No. 5, pp. 545-553.
Lauvergeat, V., et al., "Site-directed mutagenesis of a serine residue in cinnamyl alcohol dehydrogenase, a plant NADPH-dependent dehydrogenase, affects the specificity for the coenzyme," Biochemistry, 1995, vol. 34, pp. 12426-12434.
McKie, J.H., et al., "A molecular model for cinnamyl alcohol dehydrogenase, a plant aromatic alcohol dehydrogenase involved in lignification," Biochimica et Biophysica Acta, 1993, vol. 1202, pp. 61-69.
Andrieu, J., et al., "Digestibilite et valeur energetique des ensilages de mais: le point sur les methodes de prevision au laboratoire," INRA Prod. Anim., 1999, vol. 12, No. 5, pp. 391-396.
Anterola, A.M., et al., "Trends in lignin modiication: a comprehensive analysis of the effects of genetic manipulations/mutations on lignification and vascular integrity," Phytochemistry, 2002, vol. 61, pp. 221-294.
Barriere, Y., et al., "Brown-midrib genes of maize: a review," agronomie, 1993, vol. 13, pp. 865-876.
Boudet, A.M., et al., "Tansley Reveiw No. 80 Biochemistry and molecular biology of lignification," New Phytol., 1995, vol. 129, pp. 203-236.
Guillaumie, S., et al., "Differential expression of phenylpropanoid and related genes in brown-midrib bm1, bm2, bm3, and bm4 young near-isogenic maize plants," Planta, 2007, vol. 226, pp. 235-250.

*Primary Examiner* — Brent T Page
(74) *Attorney, Agent, or Firm* — Connolly Bove Lodge & Hutz LLP

(57) ABSTRACT

The Invention relates to maize having a reduced level of CAD2 activity due to the presence of the delta-314 allele, and to the use thereof for silage.

4 Claims, 2 Drawing Sheets

A.

B.

MAIZE HAVING IMPROVED DIGESTIBILITY

RELATED APPLICATIONS

This application is a national stage application (under 35 U.S.C. §371) of PCT/EP2008/059909, filed Jul. 29, 2008, which claims benefit of French application 0705601, filed Jul. 31, 2007.

The present invention relates to the field of plant improvement, in particular of the improvement of maize digestibility. Given the qualitative importance of lignin in digestibility properties, an increase in, a decrease in or a modification of the quantity and/or of the quality of lignin may have considerable industrial or agronomic consequences. The present invention relates more specifically to the development of a particular allele of the gene encoding the first isoform of cinnamyl alcohol dehydrogenase or CAD2 (EC:1.1.1.195) in maize. The presence of this allele results in a decrease in the quantity of lignin present in the plant.

Lignin is one of the two predominant components of the plant wall, with cellulose. The plant wall, which is mainly constituted of cellulose, hemicellulose and lignin, offers the cell a natural barrier against the exterior. Many studies have demonstrated that one of the responses to biotic stresses (pathogenic attacks) or abiotic stresses (drought, wind, etc.) consists of a reinforcement of the plant wall, in particular of a higher lignin content. Moreover, many agronomical or industrial sectors see their yields directly linked to the content and/or to the composition of lignin in the wall. Among these, mention may be made of paper industries, fuel production or silage production.

Consequently, it is advantageous to be able to modulate the lignin content and composition, either in order to reinforce plant walls so as to improve resistance to stresses, or, on the contrary, to weaken the plant wall in order to facilitate the extraction of cellulose or other chemical compounds (paper industry, energy production) or the digestibility of forage (Baucher et al., 1998 Plant Mol Biol 39, 437-447).

For example, the quality of silage maize can be improved by decreasing the lignin content or by modifying the lignin composition. Maize silage is an advantageous food: the yield in the field is relatively high, harvesting and storage are easy, and the nutritional qualities are stable and can easily be supplemented with proteins by means of other forage silages or by means of soybean cakes. An experiment carried out by Emile (1995, Annales de zootechnie [Annals of zootechnics]) demonstrates that feeding cattle with a more digestible maize makes it possible to increase the level of milk production by more than one kilogram per day, and weight gain by 22 kg, compared with a diet with a less digestible maize. Thus, the more digestible the variety, the more milk production is increased, with a decrease in the loss of meat. The optimization of the qualities of maize silage thus consists in increasing the net energy provided by this type of feed by improving its digestibility and therefore by reducing the lignin content.

Thus, the selecting or the attaining of more digestible maize plants, in particular in which the lignin biosensitive pathway is modified, is one of the favored main lines for improving maize. However, it is advisable for the selected plants to have good yields and to be relatively insensitive to the various stresses (mechanical, hydric, etc.).

It is, however, difficult to know how to modify the lignin biosynthesis pathway and to predict what the consequences of the modifications will be. This is because the lignin biosynthesis pathway remains a complex pathway involving a large number of enzymatic reactions (Dixon et al., 2001, Phytochemistry 57(7), 1069-1084), and for which the possible mechanisms of compensation are yet incompletely elucidated.

Lignin is considered to be an insoluble polymer of 3 monomers of alcohols or monolignols: p-coumaryl alcohol (H subunits), coniferyl alcohol (G subunits) and sinapyl alcohol (S subunits), derived from the phenylpropanoid pathway (Neish, 1968, Constitution and Biosynthesis of Lignin, eds New York, Springer Verlag 1-43). Each type of precursor can form a variety of bonds with others, and thus constitute lignin. Other bonds may also be established with other parietal compounds (polysaccharides and proteins) so as to form a complex three-dimensional network.

The main steps in lignin production are hydroxylation, O-methylation of the aromatic rings, and then conversion of the carboxyl side chain to an alcohol function.

The current hypothesis for the monolignol biosynthesis pathway considers that the metabolic network resulting in the formation of the S and G subunits involves successive hydroxylation and O-methylation reactions at various levels of oxidation of the side chain. The enzymes of the network include:
  distinct O-methyltransferases: caffeic acid 3-O-methyl-transferase (COMT), also known as 5-hydroxyconiferyl aldehyde O-methyltransferase (AldOMT) and caffeoyl coenzyme A 3-O-methyltransferase (CCoAOMT)
  hydroxycinnamate coenzyme A ligases (4CL)
  one or more cytochrome P450-dependent ferulate 5-hydroxylase(s) (F5H),
  and several isoforms of cinnamoyl CoA reductase (CCR) and of cinnamyl alcohol dehydrogenase (CAD).

The properties of these various enzymes have been the subject of reviews (Boudet et al., 1995 New Phytol. 129, 203-236; Dixon et al., 2001, cited above; Whetten et al., 1998 Annu Rev. Plant Physiol Plant Mol Biol, 49, 585-609, Li et al., 2000 J. Biol Chem, 275, 6537-6545).

For several years, attempts have been made to modify the lignin content and composition of plants by overexpressing or underexpressing one or more genes of the lignin biosynthesis pathway (Anterola and Lewis, 2002, Phytochemistry 61, 221-294). In particular, patent applications (WO 99/24561, EP0516958, WO 93/05160, WO 93/05159, WO 97/12982) disclose various strategies imagined. However, the overexpression or the underexpression of one or more enzymes does not always give constant and predictable results.

Another strategy consists in using, in the variety selection schemes, mutants of the targeted gene. For example, the natural "brown midrib" maize mutant bm3 (which has a reddish-brown coloration of the lignified tissues) has an insertion in the gene encoding COMT-AldOMT. The bm1 mutant (Jorgensen, 1931, Journal of the American Society of Agronomy 23, 549-557; Kuc and Nelson, 1964, Archives of Biochemistry and Biophysics 105, 103-113), which has been known for a long time, has for its part a mutation which colocalizes with the CAD locus (Halpin et al., Plant J. 1998, 14(5), 545-53; Guillaumie et al., Planta. 2007, 226(1), 235-50). These bm1 and bm3 maizes differ from "normal" maizes by virtue of a reduced lignin content, but their in-field yield is less. They are, in addition, more sensitive to lodging and show a lack of growth and of vigor at the beginning of vegetation and delayed flowering. All these faults prevent the exploitation thereof (Barrière and Argillier, Agronomie [Agronomics], 13, 865-876 (1993), Anterola and Lewis, cited above).

Cinnamyl alcohol dehydrogenase (CAD) is involved in the lignin biosynthesis pathway in order to convert p-coumaraldehyde, coniferaldehyde and sinapaldehyde to p-coumaryl alcohol, coniferyl alcohol and sinapyl alcohol, respectively.

At least two isoforms of the CAD enzyme have been isolated in various species (and up to 16 isoforms in *Arabidopsis*). The exact role of these various isoforms remains disputed. Some authors have proposed that these various isoforms have different affinities for the substrates mentioned above. Another hypothesis envisions different CAD isoforms depending on the cell type or the developmental stage. However, none of these hypotheses has been clearly demonstrated.

In maize, Guillaumie et al., (Planta. 2007; 226(1): 235-50) report the existence of 5 genes which are annotated cinnamyl alcohol dehydrogenase, including one type 2 gene, one type 1 gene, and 3 genes annotated cinnamyl alcohol dehydrogenase-like, and one gene annotated sinapyl alcohol dehydrogenase (which may have a similar enzymatic activity). The type 2 CAD2s appear to be more particularly involved in the lignin biosynthesis pathway. However, Guillaumie et al. show that the CAD type 1 gene also appears to be dysregulated in the bm1 mutant (mutant in the CAD type2 gene).

Patent applications WO 93/005159 and WO 98/003535 concern, inter alia, transgenic plants manipulated in terms of the maize CAD gene. These applications do not describe how to obtain maize plants having a mutated CAD gene, exhibiting improved digestibility and acceptable agronomic properties.

Those skilled in the art are thus incapable of predicting whether a specific mutation of the CAD2 gene other than the known bm1 mutation located in the locus of this gene will result in a maize that is more digestible and is of agronomic interest.

The object of the present invention is to provide those skilled in the art with a maize which actually has improved digestibility, by developing a favorable allele of CAD2 (called Δ314), the insertion of a transposon having been carried out after nucleotide 740 of the gene in SEQ ID No.1, representing an allele (cDNA) encoding this enzyme. The coding portion extends from nucleotide 73 to nucleotide 1176 of this sequence, and the insertion is located in the last exon of the gene.

The sequence of another cDNA (GenBank sequence Y13733) is represented by SEQ ID No.2, the coding portion extending from nucleotide 128 to nucleotide 1231 for this sequence. It is clear that these sequences are given only by way of example, and that those skilled in the art are capable of identifying themselves the genomic and/or mRNA sequences of CAD2 for various maize varieties.

Seeds having the Δ314 allele were deposited with NCIMB Limited, Ferguson Building, Craibstone Estate, Bucksburn, Aberdeen, Scotland, AB21 9YA, UK, on Jul. 26, 2007, according to the provisions of the Treaty of Budapest, under number NCIMB 41491.

The invention provides in particular a maize plant having said Δ314 allele.

This plant shows a disruption of the expression of the CAD2 gene and/or the enzyme encoded by this gene, such that the lignin content is decreased by at least 5%, preferably by at least 7%, more preferably by at least 10%, and the digestible fraction of the walls is increased by 5%, preferably by at least 7%, more preferably by at least 12%, compared with virtually isogenic plants which do not have this allele that leads to such an inhibition of CAD2 gene activity.

Thus, the present invention relates in particular to a maize plant exhibiting an at least 5%, preferably at least 10%, more preferably at least 15% increase in digestibility (measured by NIRS). The invention also relates to a maize plant which exhibits an at least 5%, preferably at least 10%, more preferably at least 13% increase in digestibility (measured by the IVDNSC method).

Preferably, the maize according to the invention is an "elite" maize. Those skilled in the art are well aware of the definition of an elite maize. The term "elite maize" is intended to mean a maize intended to generate hybrids intended to be marketed by crossing with another elite maize. An elite maize is defined as such in relation to the territory envisioned for the marketing, and also the agronomic characteristic(s) desired for the hybrid progeny. It is in particular a maize that can be listed in a reference catalog.

Thus, depending on whether the progeny are intended for human food or animal feed, a seed yield or a yield per hectare and good digestibility will, for example, be respectively sought when the "elite" nature "of the maize" is evaluated.

In order to determine the elite nature of a maize, hybrids obtained from said maize are compared with commercial reference hybrids (sold for the same objective in the same region), by means of field trials, by reporting and measuring agronomic characteristics appropriate for the desired objective. A maize is defined as elite if the results obtained for the parameters studied for a hybrid obtained by crossing said maize are 90% superior to the results reported for the same parameters of the reference hybrids. In the context of the present invention, the digestibility characteristic is in particular studied (digestibility measured by NIRS (near infrared spectroscopy), for example).

Near infrared spectroscopy (NIRS) is the measurement of the wavelength and the intensity of absorption of near infrared light by a sample, in the 800 nm-2.5 μm (12,500-4000 cm$^{-1}$) range. This spectroscopy is typically used for quantitative measurements of organic functional groups, in particular O—H, N—H and C═O. This method is commonly used in the analysis of sample digestibility.

Thus, an elite maize is a maize which combines the maximum of agronomic characteristics necessary for economic penetration of the targeted market. Since the maize market is today a market of hybrids, the elite nature of a maize is also evaluated by the capacity of said maize for hybrid combination/production.

Thus, the present invention preferentially relates to an elite maize intended for the marketing of hybrids for animal feed and silage, having the Δ314 allele. This elite maize is therefore homozygous for the Δ314 allele.

In another embodiment, the invention relates to a hybrid maize obtained by crossing two homozygous parent lines, said hybrid maize having a Δ314 allele. This hybrid maize may be homozygous (if each homozygous parent has the Δ314 allele) or heterozygous for the Δ314 allele.

The present invention also provides those skilled in the art with the means for selecting the maize plants having this improved digestibility characteristic. It is in fact sufficient to carry out a PCR, or a Southern blot (hybridation of genomic DNA on a membrane) in order to monitor the presence of the insertion in the last exon of the gene encoding CAD2. Those skilled in the art can easily determine the primers and probes for identifying the presence of the Δ314 allele. The invention thus also relates to a method for monitoring the Δ314 allele by molecular biology techniques, and in particular via PCR using the primers mentioned in the examples.

The invention is also the subject of a method for obtaining maize plants having improved digestibility by virtue of the Δ314 allele.

The invention also relates to a method for obtaining a maize line having increased digestibility, comprising the step of introgressing the Δ314 allele into a reference line having an agronomic characteristic of quality. The introgression of the characteristic is in particular carried out by selection, according to methods known in the art (crossing and self-pollination). The plants are in particular selected by means of molecular markers.

The principle is summarized below:

A series of backcrosses between the elite line and the line carrying the Δ314 allele (single site on chromosome 5L) is carried out.

During the backcrosses, the individuals carrying the Δ314 allele and having recombined the smallest fragment of the donor line around this allele, can be selected. In fact, by virtue of the molecular markers, the individuals having, for the markers close to the gene, the genotype of the elite gene are selected.

Furthermore, it is also possible to accelerate the return to the elite parent by virtue of the molecular markers distributed over the whole of the genome. At each backcross, the individuals having the most fragments derived from the recurring elite parent will be chosen.

With good implementation, from the fourth generation onward, it is possible to obtain a line virtually isogenic with the elite line, i.e. identical to the starting elite line, but having integrated the locus bearing the Δ314 allele.

Thus, in one preferred embodiment, said method comprises the steps consisting in:
a) crossing a first maize line exhibiting the Δ314 allele with a second maize line not exhibiting said allele,
b) genotyping the progeny obtained and selecting the progeny exhibiting the Δ314 allele having the best genome ratio with regard to said second maize line,
c) backcrossing said progeny with said second maize line,
d) repeating steps b) and c), if necessary, until a line isogenic with said second maize line, exhibiting the Δ314 allele, is obtained,
e) optionally, carrying out self-pollination in order to obtain a plant homozygous for the Δ314 allele.

The genotyping of step b) is preferably carried out using molecular markers (microsatellite markers, for example), making it possible to define the share of each of the two parents in the progeny. The maizes which have the appropriate genetic characteristic with regard to the Δ314 allele are also selected in the progeny, in a standard manner by molecular biology methods (such as PCR or Southern blot).

Surprisingly, it has been shown that the repetition of the backcrosses between the lines selected in step b) and the second maize makes it possible to achieve the appearance of a much more pronounced phenotype within said second maize.

This result is entirely surprising since one could have expected to observe an improvement in digestibility from the first crossing of the maize exhibiting the 314 allele with the second maize.

Moreover, the agronomic results observed after multiple backcrosses (5 backcrosses and 2 self-pollinations) do not show any difference between the isogenic lines exhibiting the mutation and the control plants.

Thus, those skilled in the art could not imagine being able to obtain maize having increased digestibility, with satisfactory agronomic properties, in view of the existing teaching on the bm1 mutant. They could also not have been prompted to develop a specific mutant allele in the CAD2 gene, such as that described in the present invention.

Finally, the invention relates to the use of a maize according to the invention, for preparing a composition intended for cattle feed, to a method for preparing a composition intended for cattle feed comprising the silage of a maize according to the invention, and also to the resulting composition intended for cattle feed.

Mutant plants: having the Δ314 allele; control plants: not having this allele.

Figure 3:
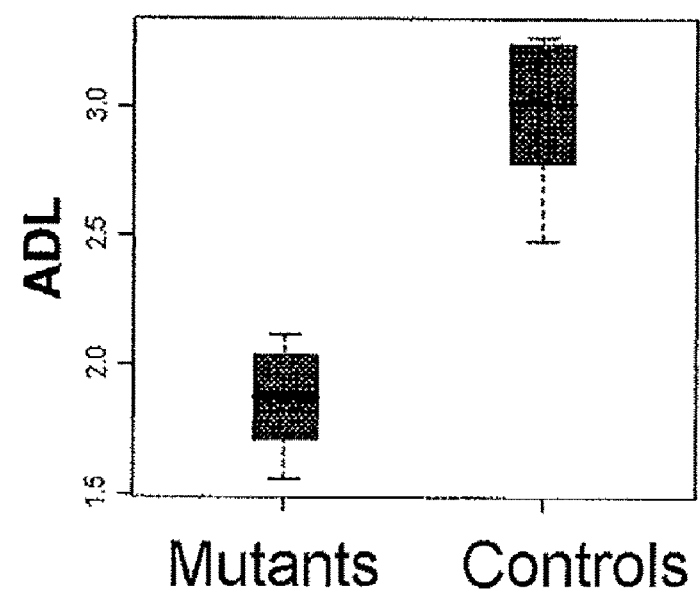
Figure 3:
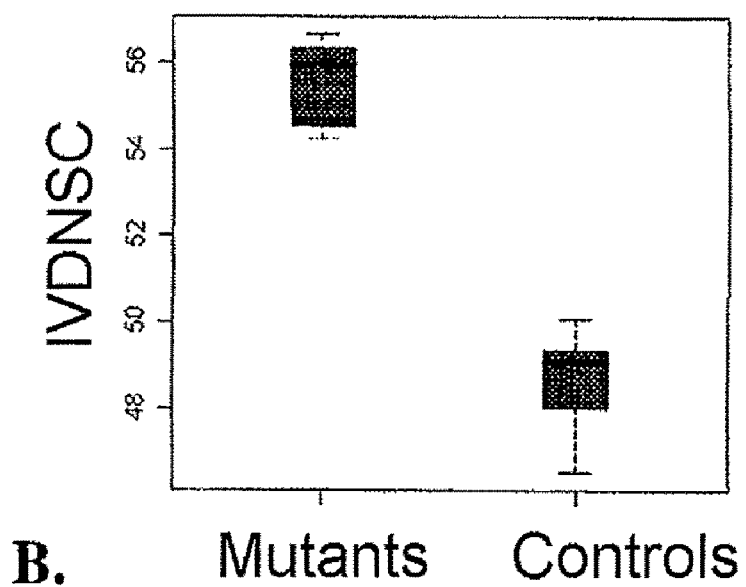

FIG. 3: Results of the introgression of the Δ314 allele on the quantity of lignin (ADL, FIG. 3.A), and the wall digestibility (IVDNSC, FIG. 3.B). Mutants: plants having the Δ314 allele; controls: plants not having this allele.

EXAMPLES

Description of a Maize Exhibiting a Modification in the CAD2 Gene

A maize line exhibiting an insertion of the mutator element at position 740 of the reference sequence SEQ ID No. 1 is isolated. The allele thus obtained is called Δ314.

In order to determine whether the insertion is in homozygous or heterozygous form, a pair of primers was defined: CAD2 15 sense primer of sequence SEQ ID No. 3: AGCACTTTGGGCTGACGAAC, upstream of the insertion, and a CCR 14 antisense primer of sequence SEQ ID No. 4: ACCATCCATCGTCTCATCTC, downstream of the insertion.

In addition to these two primers, the OMuA primer, SEQ ID No. 5: CTTCGTCCATAATGGCAATTATCTC specific for the endogenous transposable element is used. This primer is directed toward "the exterior" of the transposon.

Figure 1:
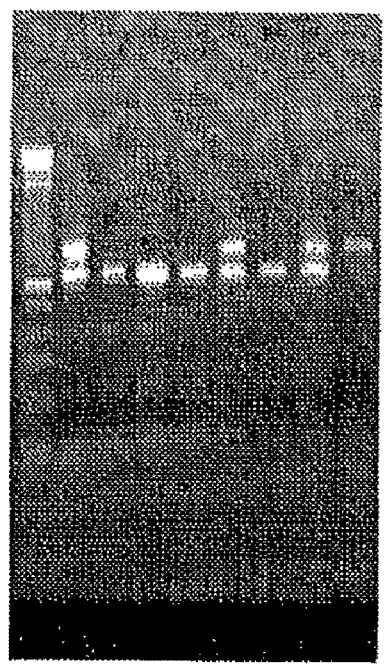
FIG. 1: Illustration of a method allowing the monitoring the introgression of the Δ314 allele. Amplification results.

These three primers can be used simultaneously in a PCR amplification experiment using genomic DNA (hybridization temperature=58° C.). Loading of the amplification products on a gel reveals:
the obtaining of a single band approximately 800 bp long for plants said to be "wild-type" of this locus (i.e. not having the mutation);
the obtaining of a band of approximately 630 bp for mutant homozygous plants, corresponding to the amplification obtained between CAD2 15 and OmuA;
or the obtaining of the two bands for heterozygous plants. These results are illustrated in FIG. 1.

The first well on the gel contains the size marker: the lowest band corresponds to 100 bp and there are 100 bp between each band.

Well 9 corresponds to a wild-type individual not carrying the Δ314 allele.

Wells 3, 4, 5 and 7 correspond to individuals which are homozygous mutants for Δ314.

Wells 2, 6 and 8 correspond to heterozygous individuals.
Backcross and Self-Pollination Scheme In order to study more precisely the effect of the insertion observed in the CAD2 gene in an elite maize, successive backcrosses are carried out with a Limagrain elite line.

This method makes it possible to very rapidly obtain virtually isogenic lines differing only by the locus bearing the modified allele, the progeny being tested for having a genome ratio as close as possible to that of the elite parent while at the same time having the allele that it is desired to introgress. These tests are aided by molecular markers (well-known techniques, microsatellites, AFLP, etc.). In order to try to assess the effect of the insertion as early as possible (obtaining of homozygous plants), self-pollinations are carried out at the various intermediate backcross stages.

Figure 2:
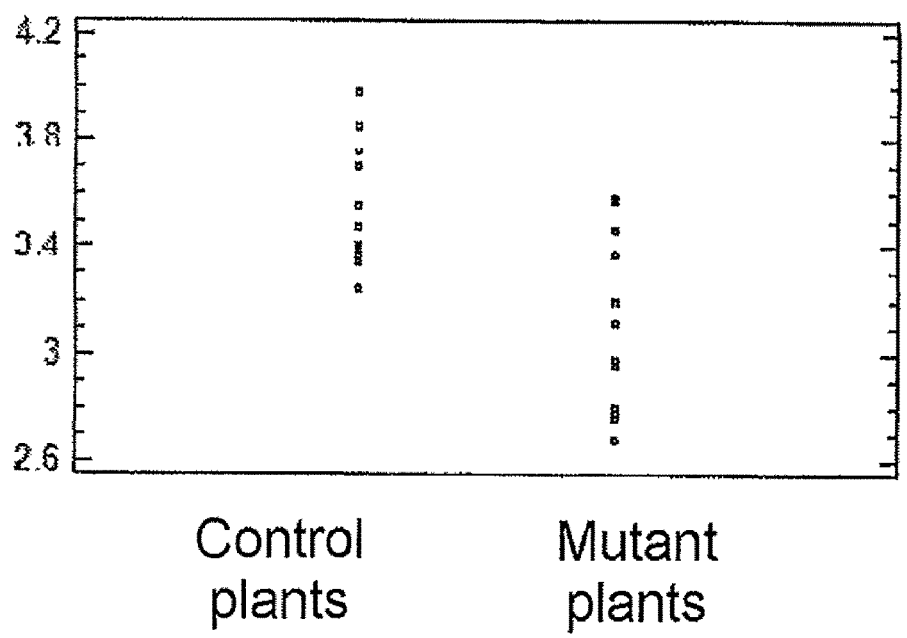
FIG. 2: NIR results of the introgression of the Δ314 allele on the quantity of lignin.

FIG. 2 shows NIR results obtained on BC2S2 plants (2 backcrosses and 2 self-pollinations).

This shows that the introgression of the Δ314 allele makes it possible to obtain a decrease in the quantity of lignin (Acid Detergent Lignin) after isolation of the walls (Neutral Detergent Fibers), according to the methods known to those skilled in the art (FIG. 2). Various methods for predicting digestibility have in particular been summarized in Andrieu et al. (INRA Prod. Anim., 1999, 12(5), 391-396).

The wall digestibility can also be assessed by measuring the IVDNSC. This criterion, proposed by Argillier and Barrière (IVDNSC, an estimation of the quality of the non seed part of silage maize on whole plant samples, Silage Maize Symposium, Nantes, Sep. 17-18, 1996), represents the digestibility of the non starch and non soluble-carbohydrate part, calculated in the following way on the basis of the enzymatic solubility of the solids content of the whole plant:

% IVDNSC=100×(% DSC−% starch−% sol. carbohydrates)/(100% starch−% sol. carbohydrates) (the DSC is the enzymatic solubility of the solids content as %, measured by the Aufrère method (in vivo digestibility and prediction of digestibility of some by-products. Feeding value of by-products and their use by beef cattle. EEC Seminar, Gontrode, September 1983, 27-29.)).

The results obtained on the BC2S2 plants are summarized in the following table:

|  | Control plants (mean) | Mutant plants (mean) |
|---|---|---|
| Lignin content = ADL | 3.5 | 3.1 |
| Digestible fraction of walls | 39.8 | 44.7 |

Other tests were carried out on BC6S2 plants (6 backcrosses and 2 self-pollinations). The results are given in FIG. 3.

It can thus be noted that the decrease in the quantity of lignins is inversely correlated with the wall digestibility: fewer lignins results in better digestibility.

Thus, the results of FIG. 3 show that the introgression of the Δ314 allele makes it possible to obtain not only a decrease in the lignin content (ADL, FIG. 3.A), but also improved wall digestibility (IVDNSC, FIG. 3.B). A decrease of close to 35% in the amount of lignins and an improvement of close to 14% in the IVDNSC can be observed.

The invention claimed is:

1. A maize exhibiting a CAD2 gene allele, called Δ314, comprising an insertion of a transposon after nucleotide 740 of SEQ ID No. 1, said allele being present in a representative sample of seeds deposited with NCIMB under number NCIMB 41491.

2. A seed of maize exhibiting a CAD2 gene allele, called Δ314, comprising an insertion of a transposon after nucleotide 740 of SEQ ID No. 1, said allele being present in the seeds deposited with NCIMB under number NCIMB 41491.

3. A method for obtaining a maize having increased digestibility, comprising the introgression of the Δ314 allele into said maize, comprising the steps consisting in:

a) crossing a first maize line exhibiting the Δ314 allele with a second maize line not exhibiting said allele, b) genotyping the progeny obtained and selecting the progeny exhibiting the Δ314 allele having the best genome ratio with regard to said second maize line, c) backcrossing said progeny with said second elite maize line that can be used for the production of hybrids, d) repeating steps b) and c), if necessary, until a line isogenic with said second maize line, exhibiting the Δ314 allele, is obtained, e) optionally, carrying out self-pollination in order to obtain a plant homozygous for the Δ314 allele.

4. A method for preparing a composition intended for cattle feed comprising the step of preparing silage using the maize as claimed in claim 1.

* * * * *

SEQUENCE LISTING

```
<160> NUMBER OF SEQ ID NOS: 5

<210> SEQ ID NO 1
<211> LENGTH: 1517
<212> TYPE: DNA
<213> ORGANISM: Zea mays
<220> FEATURE:
<221> NAME/KEY: insertion
<222> LOCATION: (740)..(741)

<400> SEQUENCE: 1
gtgcgggctc gtctccatcg cccgccaccc gctccgtcgt cgttcgtccc cgccgcgccg      60
atcccgaatc gaatggggag cctggcgtcc gagaggaagg tggtcgggtg ggccgccagg     120
gacgccaccg gacacctctc cccctactcc tacaccctca ggaacacagg ccctgaagat     180
gtggtggtga aggtgctcta ctgcgggatc tgccacacgg acatccacca ggcaaagaac     240
cacctcgggg cttcaaagta tcctatggtc cctgggcacg aggtggtcgg cgaggtggtg     300
gaggtcgggc ccgaggtggc caagtacggc gtcggcgacg tggtaggcgt cggggtgatc     360
gttgggtgct gccgcgagtg cagcccctgc aaggccaacg ttgagcagta ctgcaacaag     420
aagatctggt catacaacga cgtctacact gatggacggc ccacgcaggg tggattcgcc     480
tccaccatgg tcgtcgacca gaagtttgtg gtgaagatcc cggcaggtct ggctccggag     540
caagcggcgc cgctgctgtg cgctggcgtg acggtgtaca gcccgctgaa gcactttggg     600
ctgacgaccc cgggcctccg tggcggcatc ctgggcctcg gcggcgtggg ccacatgggc     660
gtgaaggtag ccaaggccat gggccaccac gtgacggtga tcagctcgtc gtccaagaag     720
cgcgcggagg caatggacca cctcggcgcg gacgcgtacc tagtgagctc ggacgccgcg     780
gccatggggc cggccgccga ctcgctggac tacatcatcg acacggtgcc cgtgcaccac     840
ccgctggagc cgtacctggc gctgctgaag ctggacggca gctcgtgct gctgggcgtc     900 atcggcgagc ccctgagctt cgtgtcgccc atggtgatgc tggggcggaa ggccatcacg     960
gggagcttca tcggcagcat cgacgagacc gctgaggtgc ttcagttctg cgtcgacaag    1020 gggctcaccct cccagatcga ggtggtcaag atggggtacg tgaacgaggc gctggagcgg    1080
```

```
ctggagcgca acgacgtccg ctaccgcttc gtcgtcgacg tcgccggtag caacgtcgag    1140
gcggaggcgg cggcggcgga tgcggccagc aactgatggc accgcgtcgt cgagtcgaac    1200
cacgtctgtg cgccgcgtgc aacgttcgtt cgggtcgagt ctgcgtgcaa cgttctgctt    1260
cctttactag ttgttgtctt tccgccttct tgccgttctg ttctgggctt tgagatgaga    1320
cgatggatgg tcagttttta atgtcagact gaataactac gtatagtact gtagtattac    1380
tcggagtacg ccagaatgtg gtgtggtgtc agtctcacca gcaatctgga tttgccaagt    1440
gtttctattt tttcttcggt ttgcccgagt gtttgtgatt gttaagaact acgttattac    1500
ggatcgtcaa aaaaaaa                                                   1517

<210> SEQ ID NO 2
<211> LENGTH: 1516
<212> TYPE: DNA
<213> ORGANISM: Zea mays

<400> SEQUENCE: 2
ccggcgctcg cgcggctttc tttcccaact ccgacgaagg ctagctacac caccttgtgc      60
gggctcgtct ccatcgcccg ccacccgctc cgtcgtcgtc gtccccgccg cgccgatccc     120
gaatcgaatg gggagcctgg cgtccgagag gaaggtggtc gggtgggccg ccagggacgc     180
caccggacac ctctccccct actcctacac cctcaggaac acaggccctg aagatgtggt     240
ggtgaaggtg ctctactgcg ggatctgcca cacggacatc caccaggcca gaaccacct     300 cggggcttca aagtatccta tggtccctgg gcacgaggtg gtcggcgagg tggtggaggt     360
cgggcccgaa gtggccaagt acggcgtcgg cgacgtggta ggcgtcgggg tgatcgttgg     420
gtgctgccgc gagtgcagcc cctgcaaggc caacgttgag cagtactgca acaagaagat     480
ctggtcatac aacgacgtct acactgatgg acggccacg cagggtggat cgcctccac      540 catggtcgtc gaccagaagt tgtggtgaa gatcccggcg gtctggctc cggagcaagc      600 ggcgccgctg ctgtgcgctg gcgtgacggt gtacagcccg ctgaagcact ttgggctgac     660
gaacccgggc ctccgtggcg catcctgggg cctcggcggc gtgggccaca tgggcgtgaa     720
ggtagccaag gccatgggcc accacgtgac ggtgatcagc tcgtcgtcca agaagcgcgc     780
ggaggcaatg gaccacctcg gcgcggacgc gtacctagtg agctcggacg ccgcggccat     840
ggcggcggcc gccgactcgc tggactacat catcgacacg gtgcccgtgc accaccgct      900 ggagccgtac ctggcgctgc tgaagctgga cggcaagctc gtgctgctgg gcgtcatcgg     960
cgagcccctg agcttcgtgt cgcccatggt gatgctgggg cggaaggcca tcacggggag    1020
cttcatcggc agcatcgacg agaccgctga ggtgcttcag ttctgcgtcg acaaggggct    1080
cacctcccag atcgaggtgg tcaagatggg gtacgtgaac gaggcgctgg agcggctgga    1140
gcgcaacgac gtccgctacc gcttcgtcgt cgacgtcgcc ggtagcaacg tcgaggcgga    1200
ggcggcggcg gcgatgcggg ccagcaactg atggcaccgc gtcgtcgagt cgaaccacgt    1260
ctgtgcgccg cgtgcaacgt tcgttcgggt cgagtctgcg tgcaacgttc tgcttccttt    1320
actagttgtt gtctttccgc cttcttgccg ttctgttctg ggctttgaga tgagacgatg    1380
gatggtcagt ttttaatgtc agactgaata actacgtata gtactgtagt attactcgga    1440
gtacgccaga atgtggtgtg gtgtcagtct caccagcaat ctggatttgc caagtgtttc    1500 tatttttaa aaaaaa                                                     1516

<210> SEQ ID NO 3
<211> LENGTH: 20
<212> TYPE: DNA
```

```
<213> ORGANISM: Artificial
<220> FEATURE:
<223> OTHER INFORMATION: synthetic primer CAD2 15

<400> SEQUENCE: 3
agcactttgg gctgacgaac                                              20

<210> SEQ ID NO 4
<211> LENGTH: 20
<212> TYPE: DNA
<213> ORGANISM: Artificial
<220> FEATURE:
<223> OTHER INFORMATION: synthetic primer CAD2 10

<400> SEQUENCE: 4
accatccatc gtctcatctc                                              20

<210> SEQ ID NO 5
<211> LENGTH: 25
<212> TYPE: DNA
<213> ORGANISM: Artificial
<220> FEATURE:
<223> OTHER INFORMATION: synthetic primer OmuA

<400> SEQUENCE: 5
cttcgtccat aatggcaatt atctc                                        25
```